(12) United States Patent
Henriksen

(10) Patent No.: US 9,880,091 B2
(45) Date of Patent: Jan. 30, 2018

(54) METHOD AND SYSTEM FOR ULTRASONIC CAVITATION CLEANING IN LIQUID ANALYSIS SYSTEMS

(71) Applicant: STATOIL PETROLEUM AS, Stavanger (NO)

(72) Inventor: Arne Henriksen, Stathelle (NO)

(73) Assignee: STATOIL PETROLEUM AS, Stavanger (NO)

(\*) Notice: Subject to any disclaimer, the term of this patent is extended or adjusted under 35 U.S.C. 154(b) by 339 days.

(21) Appl. No.: 14/435,693

(22) PCT Filed: Oct. 16, 2012

(86) PCT No.: PCT/EP2012/070486
§ 371 (c)(1),
(2) Date: Apr. 14, 2015

(87) PCT Pub. No.: WO2014/060023
PCT Pub. Date: Apr. 24, 2014

(65) Prior Publication Data
US 2015/0285733 A1  Oct. 8, 2015

(51) Int. Cl.
*B08B 3/12* (2006.01)
*G01N 21/15* (2006.01)
*B08B 7/02* (2006.01)
*G01N 21/85* (2006.01)

(52) U.S. Cl.
CPC ............ *G01N 21/15* (2013.01); *B08B 3/12* (2013.01); *B08B 7/028* (2013.01); *G01N 21/85* (2013.01); *G01N 2021/154* (2013.01)

(58) Field of Classification Search
CPC .................... G01N 2021/154; B08B 7/028
See application file for complete search history.

(56) References Cited

U.S. PATENT DOCUMENTS

| 6,880,402 B1 | 4/2005 | Couet et al. |
| 7,921,739 B2 | 4/2011 | Fjerdingstad et al. |
| 2009/0032733 A1 | 2/2009 | Thabeth et al. |

(Continued)

FOREIGN PATENT DOCUMENTS

| CN | 102085519 A | 6/2011 |
| EA | 1480764 A1 | 12/2004 |
| GB | 2368391 A | 5/2002 |

(Continued)

OTHER PUBLICATIONS

International Search Report and Written Opinion dated Jun. 13, 2013 (PCT/EP2012/070486); ISA/EP.

(Continued)

*Primary Examiner* — Michael Kornakov
*Assistant Examiner* — Ryan Coleman
(74) *Attorney, Agent, or Firm* — Banner & Witcoff, Ltd.

(57) ABSTRACT

A method and system for automated ultrasonic cavitation cleaning in a liquid analysis system and measurement of a process liquid contained inside a container or flowing in a process line by means of an inline or side-stream optical system. The method and system can be used in high pressure subsea conditions by means of an automated piston driven system for isolating the analysis chamber and achieving low pressure conditions inside the analysis chamber during the cavitation cleaning mode.

18 Claims, 7 Drawing Sheets

(56) References Cited

U.S. PATENT DOCUMENTS

2012/0255361 A1  10/2012  Thabeth et al.

FOREIGN PATENT DOCUMENTS

| GB | 2460668 A | | 12/2009 |
|---|---|---|---|
| JP | H02253137 | * | 10/1990 |
| JP | H02253137 A | | 10/1990 |
| WO | 2004057306 A1 | | 7/2004 |
| WO | 2009134145 A1 | | 11/2009 |
| WO | 2011128406 A1 | | 10/2011 |
| WO | 2012053898 A1 | | 4/2012 |

OTHER PUBLICATIONS

Henriksen, Arne: "Online Oil in Water Analysis, Why, Measuring Principles, Challenges and Experiences", Sep. 14, 2011.
http://www.ods-instrumentatie.nl—"ODS Specialist in Samplers * Analytical Systems" (Apr. 26, 2011).
http://www.oilinwater.com/bilder/filer, ProAnalysis Oil in Water Analyzer Brochure (May 2, 2008).

* cited by examiner

METHOD AND SYSTEM FOR ULTRASONIC CAVITATION CLEANING IN LIQUID ANALYSIS SYSTEMS

CROSS-REFERENCE TO RELATED APPLICATIONS

The present application is a U.S. National Phase of International Application No. PCT/EP2012/070486, filed on Oct. 16, 2012 and designating the United States of America. This application claims the benefit of the above-identified application which is incorporated by reference herein in its entirety.

TECHNICAL FIELD

The present invention relates generally to the field of liquid analysis methods and systems and particularly to automated maintenance of such systems. More specifically, the invention relates to automated ultrasound cavitation cleaning techniques used in automated optical liquid analysis systems for use at remote locations such as for subsea process control.

BACKGROUND ART

Ultrasonic Cleaning Technology is a well-known method for cleaning different surfaces, i.e. glass and metal surfaces. Some vendors/suppliers of online Oil-in-Water (OiW) analyzer systems used this technology or method for cleaning optical sapphire windows in direct contact with produced water. Analyzers are normally installed after a degassing tank and a Compact Flotation Unit (CFU) for monitoring oil discharges to the sea. OiW monitor vendors are continually developing cleaning technologies that can operate and work efficiently at higher water pressures. This is especially important for process applications and for subsea monitoring.

In publication WO-2009/134145-A1, an inline optical probe is shown that can be used for measuring components in a fluid contained in a pipe or container. An acoustic transducer is acoustically coupled to the probe whereby the acoustic vibrations remove fouling from the optical window. The transducer emits an acoustic signal in the range of 20-30 kHz.

Publication WO-2011/128406-A1 discloses an imaging apparatus for the detection of oil droplets and other bodies in a flowing liquid. An ultrasonic transducer can be deployed for the cleaning of the optical window. The imaging system can be used in both inline and side-stream modes but the side-stream mode is only mentioned in passing without technical constructional details defining how the system could be implemented.

The operational pressure ranges for the use of these systems are not given in either of these documents.

New industrial requirements have specified the goal that such subsea analysis methods need to be able to be deployed at pressures exceeding 50 bar ($5.0 \times 10^6$ Pa).

In general there are two different OiW monitor systems in operation, side-stream OiW systems that sample from a bypass line from the process line, and inline OiW systems where the measuring probe is placed directly in the process line. These and other similar systems have been tested by the inventor of the present invention at water-test-rigs.

For inline probe OiW monitor systems, the cleaning must be done at the inline process water pressure. For side-stream OiW monitor systems, it is possible to reduce the pressure by using two automatic control valves, so oil monitoring is done at process pressure and cleaning at low pressure, but the spill water released from the pressure reduction was collected in a pressure vessel under controlled operation. The conclusion from these tests was that existing ultrasonic cleaning systems can only operate effectively in lower water pressure applications (pressure below 20-25 bar, $2.0 \times 10^6$ Pa -$2.5 \times 10^6$ Pa), and preferably at 10 bar ($1.0 \times 10^6$ Pa) or below.

By definition, cavitation cleaning is most effective at lower pressure. Sound waves emitted from an ultrasound transducer are composed of an expansion mode and a compression mode. During the expansion mode the water molecules are pulled apart, and then are pressed together during the compression mode. If the expansion mode has sufficient energy to overcome the binding energy between the water molecules, a cavity, or bubble, is then produced. The compression mode then acts to implode the cavity which yields a gentle cleansing action to remove contaminants from surfaces. Most cleaning applications operate within the 20 kHz-250 kHz range, whereby a 25 kHz signal will produce 25,000 expansion/compression cycles per second. By example, a higher frequency will yield a smaller sized cavity and a more evenly distributed cavitation. Other factors influencing the cavitation efficiency include fluid density, viscosity, static fluid pressure and temperature. In general, if fluid density, viscosity and static fluid pressure are high, more energy is required to induce cavitation. Increasing temperature can be beneficial to point. Depending on the application, raising the temperature of the fluid or of a cleaning fluid to ca. 65-80% of its boiling point can assist in lowering the amount of energy to induce cavitation. Some ultrasound sensor systems may actually be designed to emit in the audible range, for example in the 12-20 kHz range, depending on the desired cleaning effect.

The development of such monitoring systems for subsea applications is very challenging. Although existing systems may be of adequate ability to fulfill the specifications set out for their use in lower pressure environments, of ca. 20-25 bar ($2.0 \times 10^6$-$2.5 \times 10^6$ Pa) or below, no solutions are given in the prior art that would enable one to solve the technical problem that is solved by the present invention.

SUMMARY OF THE INVENTION

Therefore, it is a main objective of the present invention to provide an improved and novel method and system for automated cleaning of optical windows in optics-based liquid analysis systems by way of ultrasonic based cavitation for use in remote, high pressure (up to and exceeding 50 bar, $5.0 \times 10^6$ Pa), subsea environments. In particular the present invention pertains to a technical solution for using ultrasonic cavitation cleaning technology independent of water pressure for an inline or side-stream Oil-in-Water (OiW) Monitoring System for use in subsea process control.

The above mentioned deficiencies and uncertainties associated with the prior art are rectified by way of the following novel improvements.

A first aspect of the present invention relates to a method for ultrasonic cavitation cleaning of an optical window in an analysis system in a process line containing process liquid, comprising the following steps:
isolating an optical window of a tranducer module from the process line;
reducing the liquid pressure in contact the optical window;
subjecting the optical window to ultrasonic signals;
suspending the ultrasonic signals after a given period;

increasing the liquid pressure in contact with the optical window until it is substantially the same as the liquid pressure in the process line; and reconnecting the optical window to the process line.

A second aspect of the present invention relates to the method of the first aspect, wherein the optical window is isolated from or reconnected to the process line by means of closing or opening a valve in combination with moving tranducer module by means of motors.

A third aspect of the present invention relates to the method of the first or second aspect, wherein the process liquid pressure in the process line is above $2.0 \times 10^6$ Pa, wherein the pressure of the liquid in contact with the optical window is $1.0 \times 10^6$ Pa or below during ultrasonic cavitation cleaning, wherein the said pressure of the liquid in contact with the optical window is reduced or increased by means of a piston.

A fourth aspect of the present invention relates to the method of the first aspect, wherein some of said process liquid is redirected into a side-stream flow arrangement comprising the following steps:

feeding the process liquid, having a process liquid pressure of p1, from process line by means of an inlet, through a first non-return valve, a first three-way valve, a chamber, a second three-way valve, a second non-return valve and back into the process line by means of an outlet wherein the process liquid has a pressure p2;

isolating the chamber by means of the two three-way valves;

reducing the liquid pressure p4 inside the chamber by means of piston system;

subjecting the optical window to ultrasonic signals;

suspending ultrasound signals within the chamber after a given period;

increasing the liquid pressure inside the chamber to pressure p3 in the chamber by means of piston system;

opening the chamber by means of the two three-way valves; and feeding process liquid inside chamber back to process line via the second three-way valve, the second non-return valve and the outlet.

A fifth aspect of the present invention relates to the method of the fourth aspect, wherein the process liquid pressure p1 is above $2.0 \times 10^6$ Pa and the liquid pressure p4 inside the isolated chamber is $1.0 \times 10^6$ Pa or below during ultrasonic cavitation cleaning A sixth aspect of the present invention relates to the system of the fourth or fifth aspect, wherein a cleaning agent is fed from a container to analysis chamber via the first three-way valve.

A seventh aspect of the present invention relates to the system of the fourth or fifth aspect, wherein a fluid from the analysis chamber is fed to a spill tank or pressure vessel via the first three-way valve.

An eighth aspect of the present invention relates to the method of the first aspect, wherein, some of said process liquid is rediected into a side-stream flow arrangement, wherein the process liquid is isokinetically sampled comprising the following steps:

positioning of liquid analysis system with isokinetic coaxial sampling probe into a sampling port of subsea process line by means of an ROV;

sampling from process liquid line through isokinetic coaxial sampling probe;

feeding of process liquid to a first flow controller circulation pump, a two-way valve, chamber, a three-way valve, a second flow controller circulation pump;

sealing the chamber by means of valves;

reducing the pressure inside the chamber by means of piston system;

subjecting the optical window to ultrasonic signals;

suspending ultrasound signals within the chamber after a given period;

increasing the pressure inside the chamber by means of piston system;

opening chamber by means of valves;

feeding process liquid inside chamber back to process line via valve, flow controller circulation pump and the outlet of isokinetic coaxial sampling probe; and retracting the liquid analysis system with isokinetic coaxial sampling probe from a sampling port of subsea process line by means of an ROV.

A ninth aspect of the present invention relates to the method of the eighth aspect, wherein the process liquid pressure is above $2.0 \times 10^6$ Pa and the liquid pressure inside the sealed chamber is $1.0 \times 10^6$ Pa or below during ultrasonic cavitation cleaning A tenth aspect of the present invention relates to the method of the first to the ninth aspect, wherein the measured optical properties in the process liquid are oil concentration, suspended solids, suspended oil, particulate matter and particle size.

An eleventh aspect of the present invention relates to a system for ultrasonic cavitation cleaning of an optical window in an analysis system in a process line containing process liquid comprising:

a transducer module with an optical window located adjacent to process line and in association with a chamber;

at least one valve which isolates said chamber from said process line when closed;

a piston connected to said chamber such that when the pressure in said chamber is reduced when the at least one valve, is closed and the piston is moved from a first position to a second position;

wherein the optical window is located inside or can be moved into said chamber such that the optical window of the transducer module can be subjected to ultrasonic emission from said transducer module when the pressure is reduced in said chamber.

A twelfth aspect of the present invention relates to the system of the eleventh aspect, wherein the process liquid pressure in process line is above $2.0 \times 10^6$ Pa and the pressure inside said isolated chamber is $1.0 \times 10^6$ Pa or below during ultrasonic cavitation cleaning.

A thirteenth aspect of the present invention relates to the system of the eleventh aspect, wherein some of said process liquid is redirected by means of a side-stream flow arrangement comprising:

an inlet from the process line having a liquid pressure p1 at inlet;

a feed line from inlet via to a first non-return valve, a first three-way valve, to an chamber having a pressure p3;

a transducer module connected to chamber;

a second three-way valve downstream from chamber, a piston system;

a feed line connecting a second three-way valve to a second non-return valve and back into the process line by means of an outlet wherein the process liquid has a pressure p2 at outlet, and the pressure drop from p1 to p2 is equal to p3;

wherein said transducer module comprises an optical window, an ultrasonic transducer, a fiber optic cable and a power cable connected to sensor module comprising at least one light source, a computer, an imaging camera, a UV/fluorescence spectrometer, and a cable for remote communication.

A fourteenth aspect of the present invention relates to the system of the thirteenth aspect, wherein a feed line from a cleaning agent container is connected to the analysis chamber via the first three-way valve.

A fifthteenth aspect of the present invention relates to the system of the thirteenth aspect, wherein a feed line to a spill tank or pressure vessel is connected to the analysis chamber via the first three-way valve.

A sixteenth aspect of the present invention relates to the system of the eleventh aspect, wherein some of said process liquid is redirected by means of an isokinetically sampled side-stream flow arrangement comprising:

a retractable isokinetic coaxial sampling probe with an inlet extending into a sampling port of subsea process line by means of an ROV;

a first flow controller circulation pump downstream from the sampling probe, followed by a cleaning-mode bypass channel, a two-way valve, analysis chamber with optical window, a three-way valve, a variable control piston system, a second flow controller circulation pump;

a feed line back to the sampling probe with an outlet to the process line; and a module with an ultrasound transducer, a full scan fluorescence spectrometer, microscope, video imaging camera, light sources, hardware for automatic control of the whole system and PC remote control from top-side, a cable for connection to top-side.

A seventeenth aspect of the present invention relates to the system of the sixteenth aspect, wherein a piston system is mechanically coupled to the analysis chamber, is situated directly opposite from the optical window; and a second two-way valve is situated directly downstream from the analysis chamber.

An eighteenth aspect of the present invention relates to the system of the seventeenth aspect, wherein a pressure gauge is mechanically coupled to the analysis chamber and located between two-way inlet and outlet valves of the analysis chamber.

BRIEF DESCRIPTION OF THE DRAWINGS

The invention will be described in detail with reference to the attached figures. It is to be understood that the figures are designed solely for the purpose of illustration and are not intended as a definition of the limits of the invention, for which reference should be made to the appended claims. It should be further understood that the figures are not necessarily drawn to scale and that, unless otherwise indicated, they are merely intended to schematically show the procedures described therein.

DETAILED DESCRIPTION OF THE INVENTION

Figure 1:
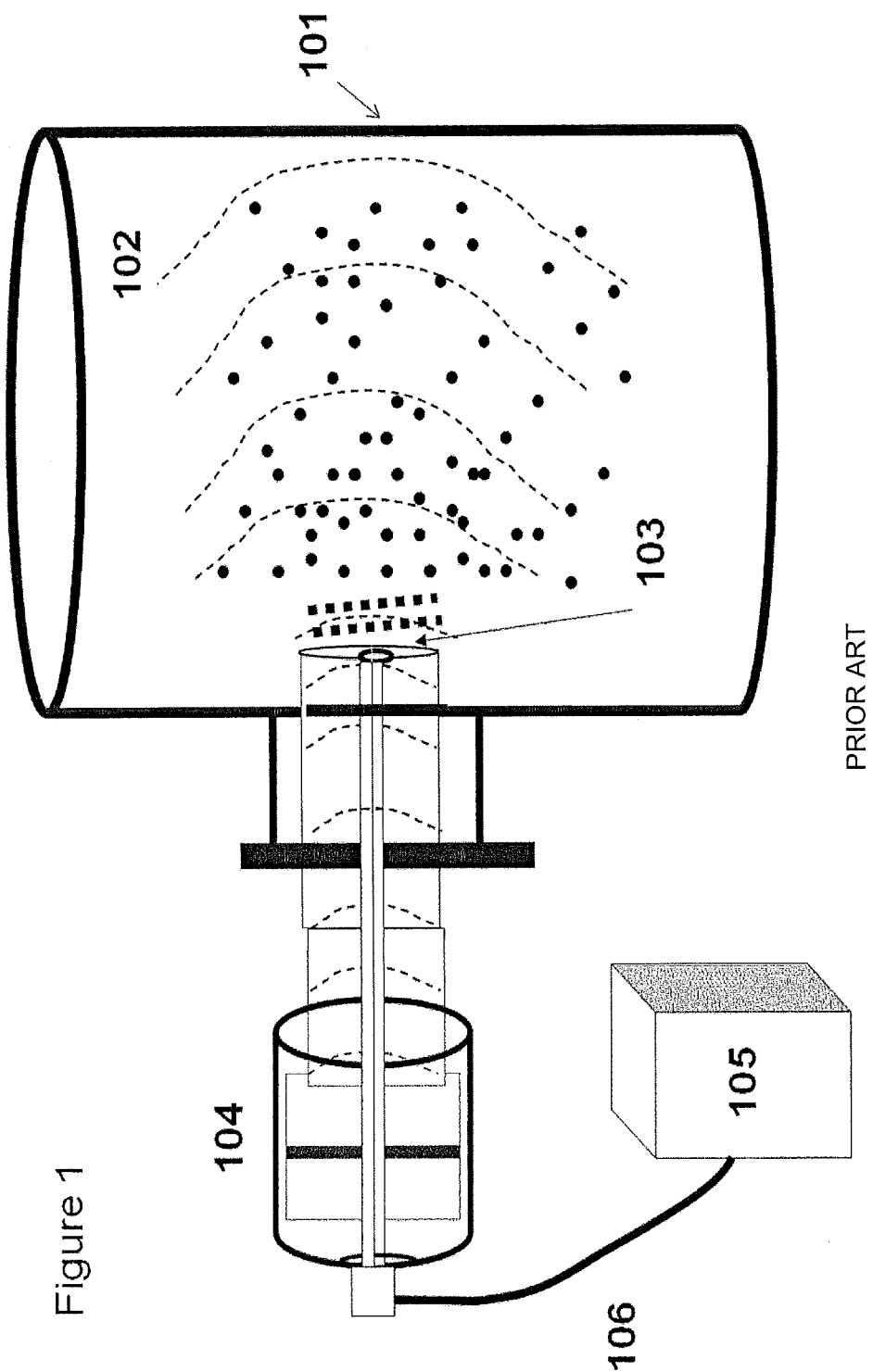
FIG. 1 shows a prior art subsea inline OiW monitor system.

The aim of the present invention to provide an improved and novel method and system for automated cleaning of optical windows in optics-based liquid analysis systems by way of ultrasonic based cavitation for use in remote, high pressure, subsea environments.

In the years preceding 2008/2009, a main focus for OiW sensors had been the measurement of lower oil concentrations (<100 ppm) in produced water discharges from platforms. At present, the assignee of the present invention has ca. 25 installations, but all of these measurement systems are installed in low water pressure applications, less than 10 bar ($1.0 \times 10^6$ Pa). In 2008/2009 a project was created targeting the development of OIW measurement systems for subsea applications which included tougher requirements for measurement systems. The key requirements are that the measurement systems must operate "maintenance free" at a process pressure of 50 bar ($5.0 \times 10^6$ Pa) at oil-in-water concentrations from 100 to 2000 ppm and of course be robust in difficult and remote locations.

At present these is a lack of OiW measuring systems having the capability of both automatic ultrasonic cleaning that also work at a water pressure of 20 bar ($2.0 \times 10^6$ Pa) (present requirements >50 bar, $5.0 \times 10^6$ Pa). In addition there is also a lack of systems that employ other types of automatic cleaning technologies that fulfill these strict requirements.

From development tests conducted in test-rigs, as mentioned briefly in the background art section, a prototype inline OIW analyzer from an established sensor manufacturer was tested. The analyzer was designed and built to perform measurements at process pressure of 50 bar ($5.0 \times 10^6$ Pa) and a total pressure limit up to 120 bar ($1.2 \times 10^7$ Pa), but automatic ultrasonic purification, cavitation, is performed at low pressure, at 10 bar ($1.0 \times 10^6$ Pa) or below. This was accomplished by closing off of the water volume in the measuring chamber by means of two valves, and opening one valve for pressure reduction whereby the water was collected in a pressure vessel. For each cleaning cycle the pressure was increased in the vessel, but it was drained when it reached 20 bar ($2.0 \times 10^6$ Pa).

The present invention is thus based on the realization that a reduction in pressure within the measuring chamber could be achieved by volume expansion by automated mechanical means. Specifically, the regulation of pressure, by volume expansion or contraction, could be accomplished by means of a piston pump, screw pump or bellows pump. What is important is that the water pressure is reduced to below 10 bar ($1.0 \times 10^6$ Pa) for ultrasonic cavitation cleaning Thus the water pressure remains equal to the process pressure when the pump pushes the piston back into its original position. The invention can thereby use ultrasonic "cavitation" cleaning technology independent of the process water pressure. This innovative method and system encompasses the following advantages and elements compared to the prior art:

as it is a closed system, there is no water discharge during operation, water pressure in the closed chamber is controlled during both decreasing and increasing pressure operation modes, the valve(s) used in the system will only operate with a very small pressure difference between process pressure and measurement chamber pressure during opening and closing. This in turn results in less stress on the ball valves at the inlet and outlet of the measuring chamber, ultrasonic cavitation cleaning is done efficiently at low water pressure, the system is operable independent of the water pressure which is especially imperative for subsea measurement applications, the invention can be implemented for both side-stream (bypass) and inline OiW monitoring modes, and all movable components are automated by way of PC/software/hardware.

As mentioned above, the present invention can be operated in either inline or side-stream mode. Described in the following is the basic principle of the method which is applicable to both modes and their variations.

Basic Method:

The central idea for the invention is to perform controlled pressure regulation by using a pressure piston in a defined closed water sample cell volume, or "analysis chamber" or merely "chamber":

1. Decrease the water pressure by moving (retracting) a piston (i.e. hydraulic, screw type or bellows type) connected to the chamber, so the chamber volume increases and the pressure drops to 10 bar ($1.0 \times 10^6$ Pa) or below.
2. Ultrasonic cavitation cleaning is performed at low water pressure.
3. The water pressure in the chamber is then increased to the process pressure by moving the piston towards its original position.

By using a controllable piston and a pressure controller for increasing/decreasing the water pressure in the chamber, there will be no water spillage, and it can operate independent of the process water pressure. By way of clarity, the use of the term "chamber" relates to a chamber where pressure is varied for the purpose of cavitation cleaning of an optical window at lowered pressure for inline embodiments, according to the present invention. For side-stream embodiments, according to the present invention, the use of the term "chamber" relates to a chamber where pressure is varied for the purpose of cavitation cleaning of an optical window at lowered pressure and for an analysis chamber for the analysis of process liquid at higher pressures. In general the length of time for the cavatition cleaning cycle is based on a standard time, based on previous experience for a given process liquid composition with regards to propensity to fouling of an optical window. And, although a main aspect of the present invention relates to cavitation cleaning of an optical window at low pressure, it should also be understood that it also relates to the sampling and analysis of process liquid at high pressure.

An example of a prior art configuration, as given in FIG. 1, shows an inline probe OiW monitor system installed in a process line 101. The dashed lines illustrate sound or ultrasonic waves 102 creating cavitation (vacuum bubbles) for removing scale particles at the optical glass surface, or window, 103. The system includes an ultrasonic transducer 104, a laser source, detector, power source located in module 105 and fiber optic cable 106. This prior art system does not have the ability to perform automated cavitation cleaning in high pressure processes.

Figure 2:
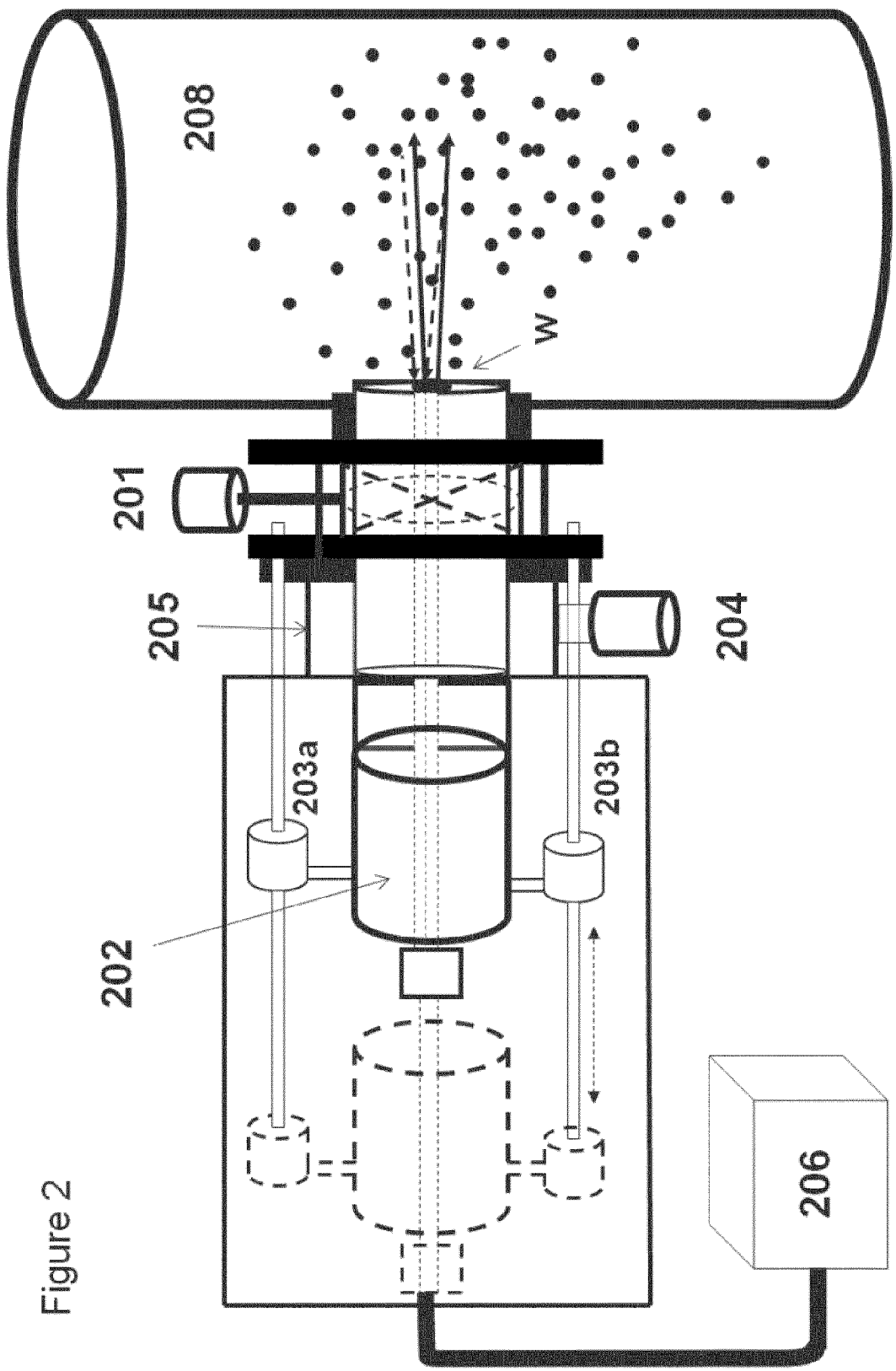
FIG. 2 shows a subsea inline OiW monitor system, in measurement mode, according to the present invention.

FIG. 2 shows a principal drawing of a subsea inline retractable probe OiW monitor system according to an embodiment of the present invention. FIG. 2 shows the placement of components during measurement mode. The light or laser source may emit in the ultraviolet (UV), visible, near infrared (NIR), infrared (IR), depending on the type of spectrograph detector and the chemical compounds of interest. For example, for the quantification of oil concentration, a full scan fluorescence spectrometer may be deployed. Depending on the optical range of the analysis system, the optical window may be made from a variety of substrate material such as UV Fused Silica, Calcium Fluoride ($CaF_2$), Magnesium Fluoride ($MgF_2$), Potassium Bromide (KBr), sapphire, Silicon (Si), Sodium Chloride (NaCl), Zinc Selenide (ZnSe), or Zinc Sulfide or other known in the art. For the embodiments according to the present invention, a sapphire optical window is most commonly used. For the detection of suspensions or the analysis of solids, oil and particle sizes, a microscope and/or a video imaging camera may be installed. The components represented in FIG. 2 include a valve 201 in the open position, an ultrasound transducer module 202, motors 203a, 203b for retracting transducer module, piston 204 for variable volume and pressure control, a chamber 205 for use during cleaning mode, a module 206 containing the OiW monitor, light source, detector and associated hardware, a sapphire optical window W during measurement mode and flowing process water inside a pipeline 208 or non-flowing process water in a container.

Figure 3:
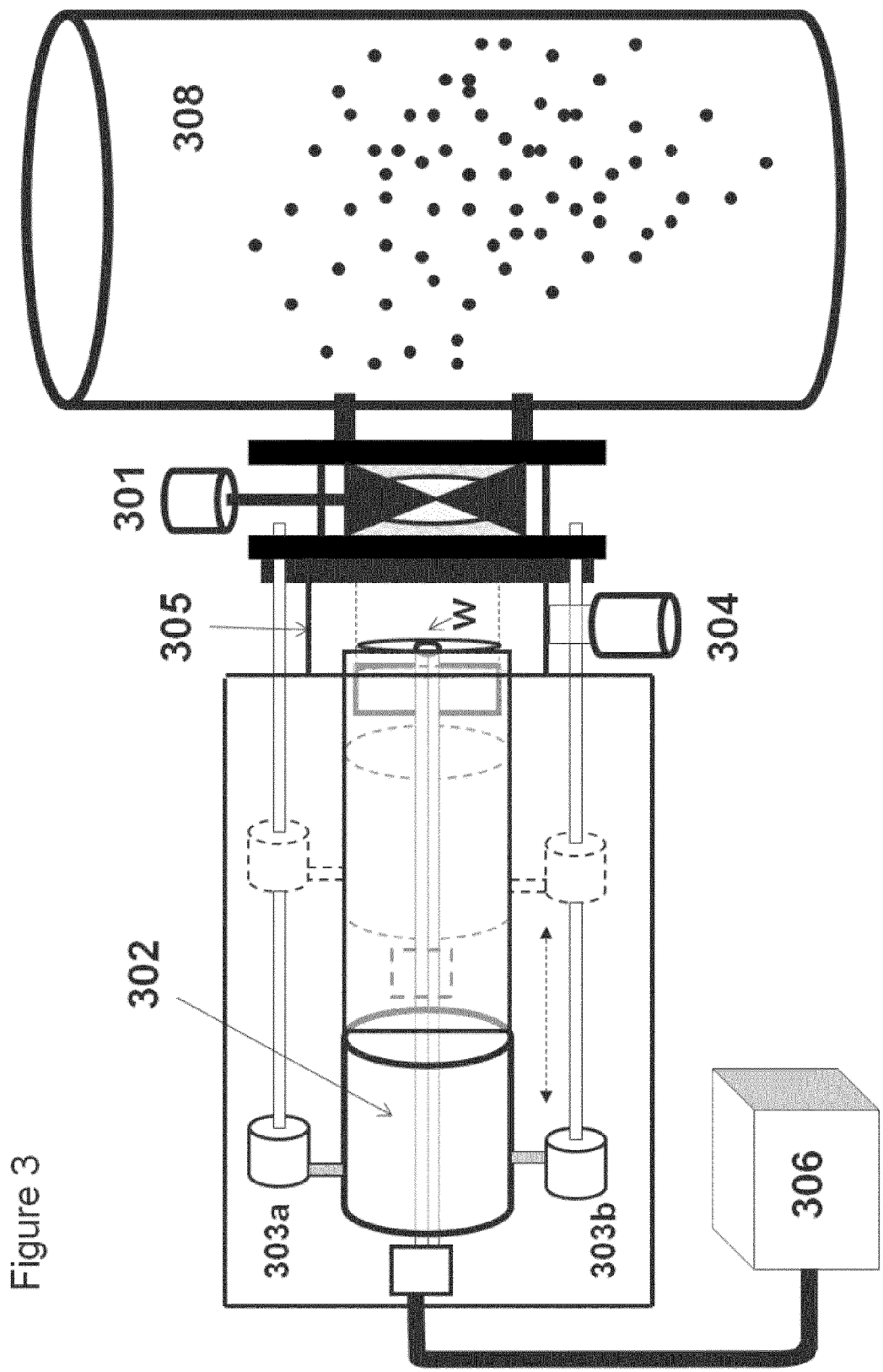
FIG. 3 shows a subsea inline OiW monitor system, according to FIG. 2, in retracted cleaning mode according to the present invention.

For the purpose of illustration, FIG. 3 shows the same system and components as in FIG. 2 when it is in the retracted position for ultrasonic cleaning with similar numbering for consistency. The optical window W is retracted within the low pressure closed chamber 305 while undergoing cavitation cleaning at low pressure. The system being comprised of a valve 301 in the closed position during cavitation cleaning mode, an ultrasound transducer module 302 in the retracted position, motors 303a and 303b for retracting transducer module 302, a piston 304 for variable volume and pressure control for the chamber 305 during cleaning mode, a module containing the OiW monitor, light source, detector and associated hardware and a pipeline 308 or container flowing or non-flowing process water inside. After cleaning, the pressure is again increased to the process pressure and the optical system is moved back into the measurement position, as in FIG. 2. A main feature of FIG. 3 is that the sapphire optical window W is located within the chamber 305. This inline probe OiW monitor system requires only one automatically controlled valve 301.

Figure 4:
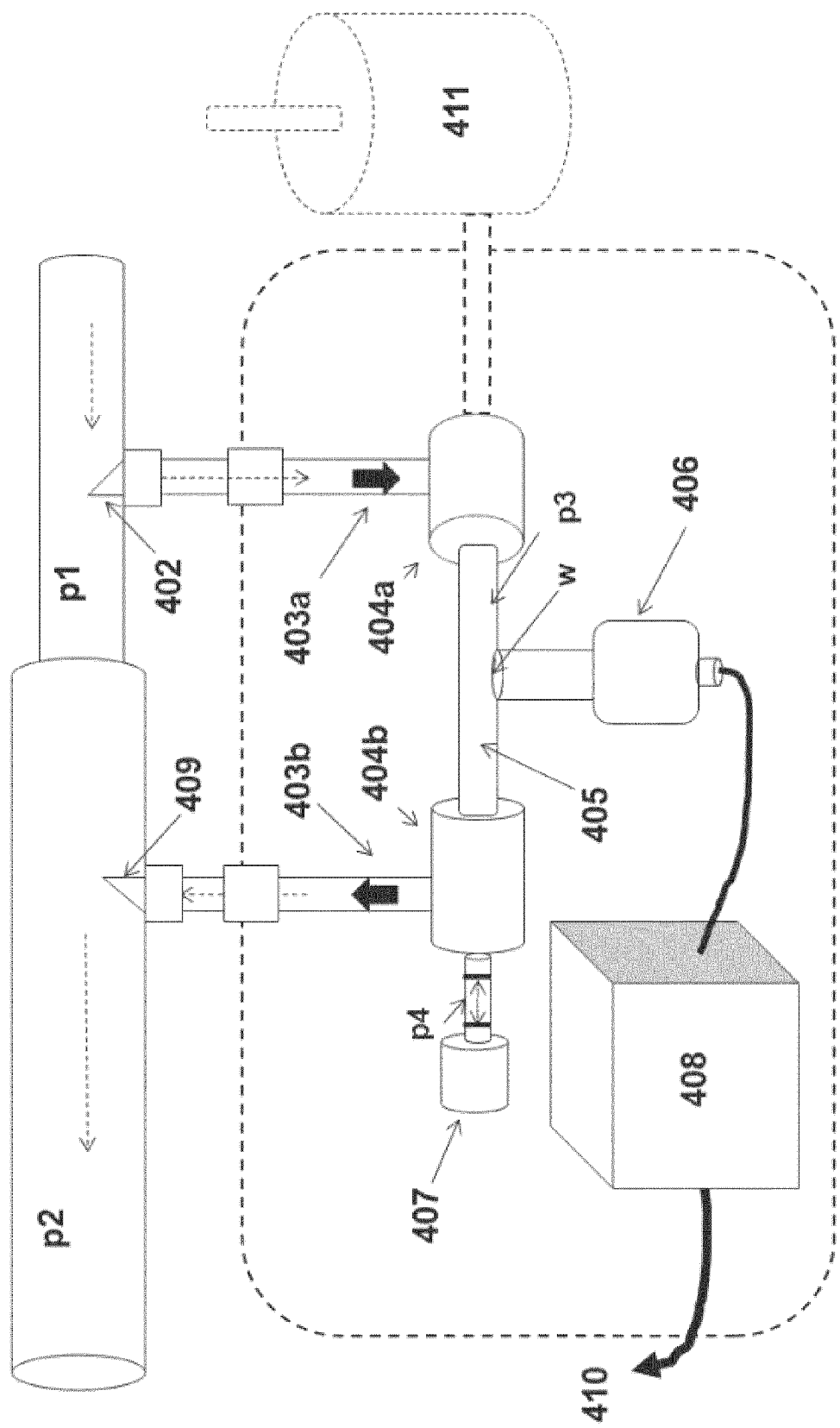
FIG. 4 shows a subsea or top-side side-stream OiW monitor system.

FIG. 4 shows a side-stream OiW monitor system according to another embodiment of the present invention that can be used either subsea or top-side. The subsea embodiment is shown within the stippled line. This embodiment includes an automated system for increasing and decreasing the sampling volume and thereby regulating the pressure inside the analysis chamber. This side-stream embodiment enables isokinetic sampling of the fluid stream. The system as shown in FIG. 4 comprises the following components: a process line 401 where the liquid pressure p1 is greater than pressure p2 and pressure p3 is the pressure in the analysis chamber during the measurement mode and is equal to the pressure difference [p1–p2], and pressure p4 is the pressure at a defined low pressure during cavitation cleaning of optical window W. An inlet 402 feeds the liquid from the process line into the analysis system. The process liquid is fed via non-return valve 403a and three-way ball valve 404a into the analysis chamber 405, further to a second three-way ball valve 404b, a second non-return valve 403b and back into the process line via outlet 409. Module 406 comprises an ultrasound transducer and sapphire optical window and is connected via a fiber optic and power cable to an analysis module 408 comprised of UV/Fluorescence spectrometer, imaging camera, computer, and light sources. Piston 407 is for volume and pressure control in the analysis chamber 405. Analysis module 408 is connected to top-side via cable 410.

An optional fluid container 411 containing chemicals such as cleaner agent, or a spill tank or a pressure vessel can be installed in fluid connection with three-way ball valve 404a.

The optical system (408) of this embodiment can be of the same type as referred to in the previous embodiments as shown in FIGS. 2 and 3. This embodiment of the present invention can also be retrofitted to a top-side measurement system by installing a connection to a spill tank, or pressure vessel 411, from three-way ball valve 404a. In another embodiment, a cleaning agent may be stored in a container 411 for use during the cleaning mode. This could be also envisioned for the subsea embodiment.

Figure 5:
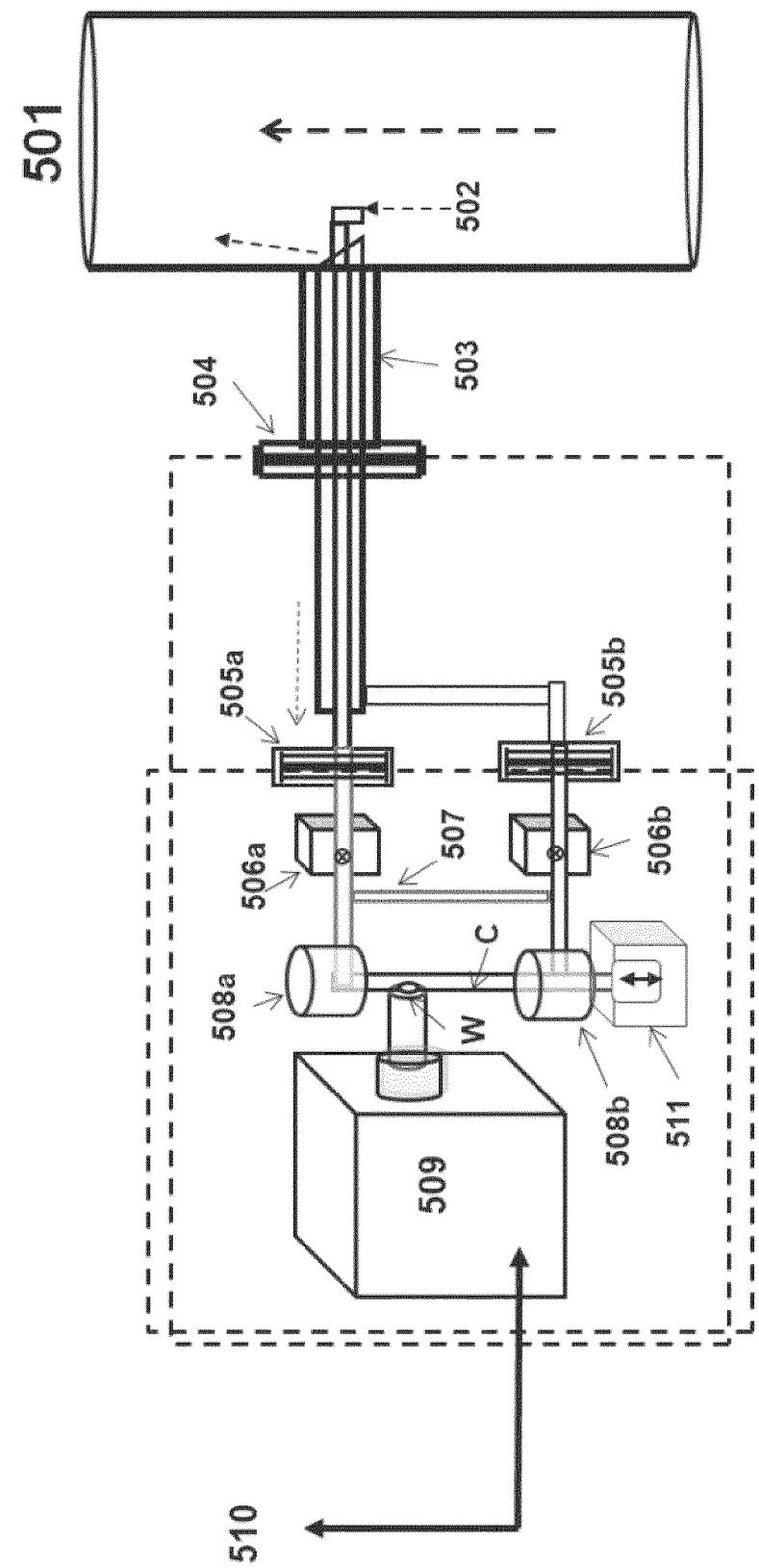
FIG. 5 shows a subsea side-stream OiW monitor system for isokientic sampling and retractable by ROV according to the present invention.

FIG. 5 shows a subsea side-stream OiW monitor system, according to another embodiment of the present invention, configured for isokinetic sampling and is retractable by way of an ROV (remotely operated vehicle) as shown by the stippled lines in two different sampling embodiments. In FIG. 5, inlet flange 504 for connection to the process line 501 is used in one possible embodiment of the present invention wherein process water is sampled through the single flange 504 and probe 503 with coaxial inlet flow channel 502 an a output flow channel back into the process line 501. In another embodiment of the present invention, flanges 505a and 505b show an ROV rectractable isokinetic sampling inlet and outlet in the case where the process line 501 has two ports. Furthermore, FIG. 5 shows the other components according to the present invention: circulation pumps/flow controllers 506a, 506b for correct water flow for isokinetic sampling, a bypass flow pathway 507 during ultrasonic cavitation cleaning of optical window W at low pressure, an inlet two-way valve 508a, an outlet three-way valve 508b, a module 509 with an ultrasound transducer, a full scan fluorescence spectrometer (oil concentration), microscope, video imaging camera (for analysis of solids, oil and particle sizes), light sources, hardware for automatic control of the entire system and PC remote control from top-side, a cable 510 for connection to top-side, a control system 511 for variable volume and pressure (piston, screw or hydraulic), an analysis chamber C and a sapphire optical window W.

Figure 6:
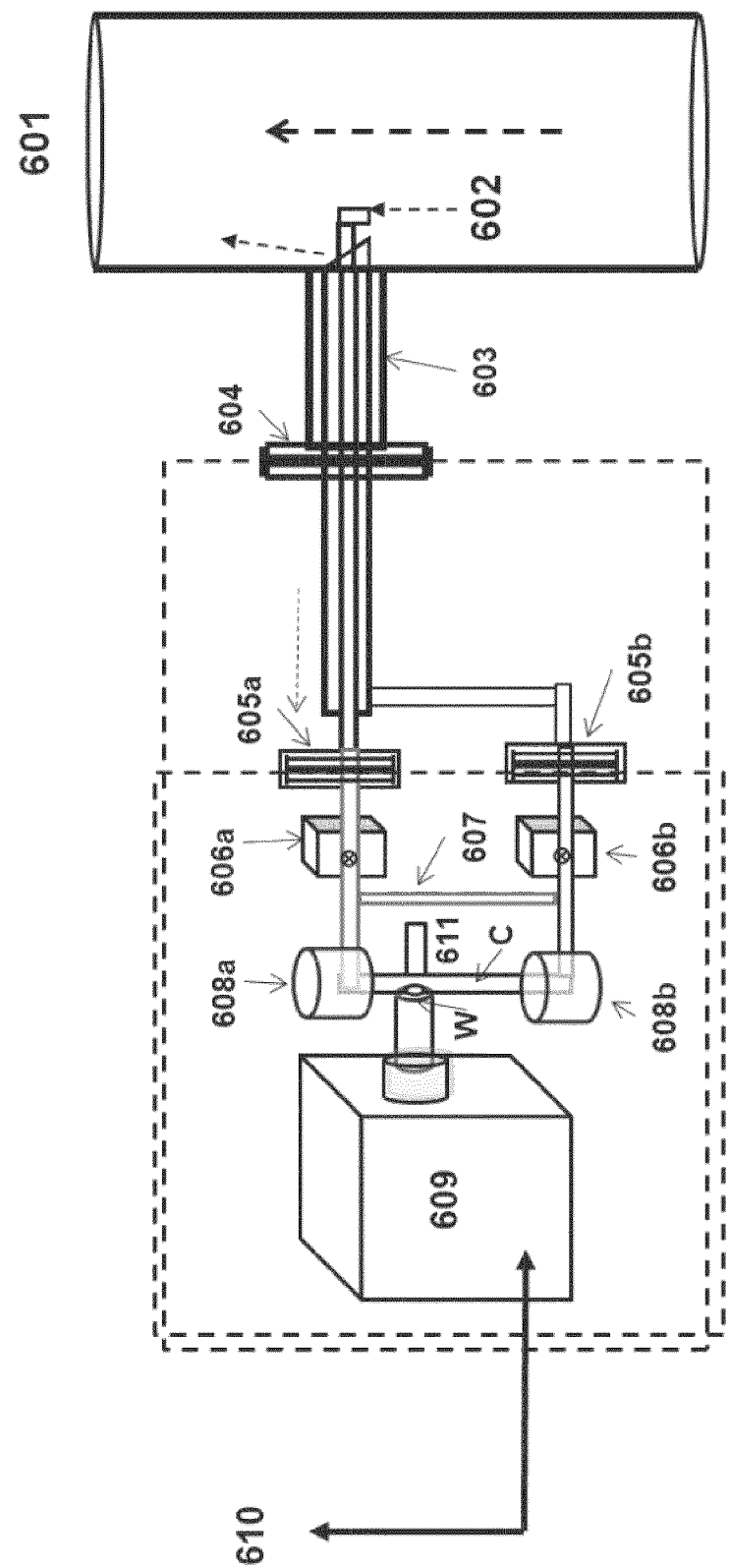
FIG. 6 shows a subsea side-stream OiW monitor system for isokientic sampling and retractable by ROV according to the present invention.

The further embodiment of the present invention as given in FIG. 6 shows the same system as in FIG. 5, with the exception of the position of the variable pressure and volume control system. In FIG. 6 a piston system 611 is connected directly to the analysis chamber C directly opposite from the sapphire optical window W. Otherwise, and for the purpose of illustration, FIG. 6 shows the same system and components as in FIG. 5 with similar numbering for consistency. For the sake of completeness, FIG. 6 shows the other components according to the present invention: circulation pumps/flow controllers 606a, 606b for correct water flow for isokinetic sampling, a bypass flow pathway 607 during ultrasonic cavitation cleaning at low pressure, an inlet two-way valve 608a, an outlet two-way valve 608b, a module 609 with an ultrasound transducer, a full scan fluorescence spectrometer (oil concentration), microscope, video imaging camera (for analysis of solids, oil and particle sizes), light sources, hardware for automatic control of the whole system and PC remote control from top-side, a cable 610 for connection to top-side, a control system 611 for variable volume and pressure (piston, screw or hydraulic), an analysis chamber C and a sapphire optical window W. In addition, the flow system comprises the process line 601, an inlet for isokinetic sampling 602, an isokinetic sampling probe 603, a flange connection 604 to process line for one ROV sampling embodiment, and flange connections 605a, 605b to process line for another ROV sampling embodiment.

Figure 7:
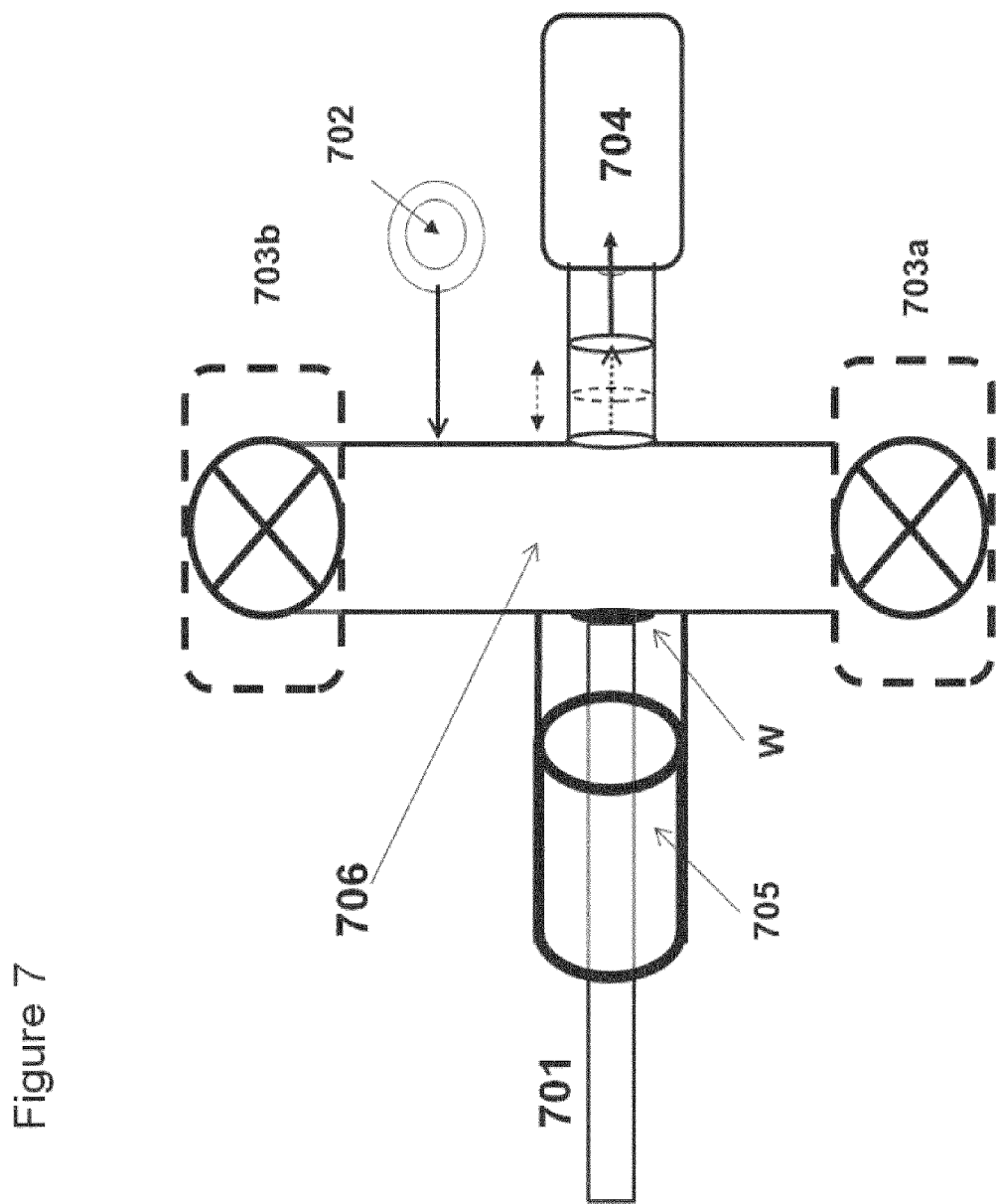
FIG. 7 shows the pressure control system as used in the system shown in FIG. 6 in more detail.

FIG. 7 shows an alternative pressure and volume control system 704 for direct coupling to the analysis chamber. The other components according to this embodiment comprise an fibre optic cable 701 from and to the analysis instruments, a pressure gauge 702, a two-way ball valve 703a on the inlet side, a two-way ball valve 703b on the outlet side, a piston device 704, typically a screw or hydraulic driven piston, an ultrasonic transducer device 705, an analysis chamber 706 and a sapphire optical window W.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the scope of the appended claims. While the invention has been illustrated and described in detail in the drawings and foregoing description, such illustration and description are to be considered illustrative or exemplary and not restrictive and it is not intended to limit the invention to the disclosed embodiments. The mere fact that certain measures are recited in mutually different dependent claims does not indicate that a combination of these measures cannot be used advantageously. Any reference signs in the claims should not be construed as limiting the scope of the invention.

The invention claimed is:

1. A method for ultrasonic cavitation cleaning of an optical window in an analysis system in a process line containing process liquid, comprising the following steps:
    isolating an optical window (W) of a transducer module from the process line;
    reducing the liquid pressure in contact with the optical window (W);
    subjecting the optical window (W) to ultrasonic cleaning by subjecting the optical window (W) to ultrasonic signals after performing the step of reducing the liquid pressure in contact with the optical window;
    suspending the ultrasonic signals after a given period;
    increasing the liquid pressure in contact with the optical window (W) until it is substantially the same as liquid pressure in the process line;
    reconnecting the optical window (W) to the process line after performing the step of increasing the liquid pressure in contact with the optical window (W) until the pressure is substantially the same as the liquid pressure in the process line.

2. Method according to claim 1, wherein the optical window (W) is isolated from or reconnected to the process line by means of closing or opening a valve in combination with moving the transducer module by means of motors.

3. Method according to claim 1, wherein the process liquid pressure in the process line is above $2.0 \times 10^6$ Pa, wherein the pressure of the liquid in contact with the optical window (W) is $1.0 \times 10^6$ Pa or below during ultrasonic cavitation cleaning, wherein the said pressure of the liquid in contact with the optical window (W) is reduced or increased by means of a piston.

4. Method according to claim 1, Wherein some of said process liquid is fed into a side-stream flow arrangement comprising the following steps;
feeding the process liquid, having a process liquid pressure of p1, from process line by means of at inlet, through a first non-return valve, a first three-way valve a chamber, a second three-way valve, a second non-return valve and back into the process line by means of an outlet wherein the process liquid has a pressure p2;
isolating the chamber by means of the two three-way valves;
reducing the liquid pressure p4 inside the chamber by means of piston system;
subjecting the optical window (W) to ultrasonic signals;
suspending ultrasound signals within the chamber after a given period;
increasing the liquid pressure inside the chamber to pressure p3 in the chamber by means of piston system;
opening the chamber by means of the two three-way valves; and
feeding process liquid inside chamber back to process line via the second three-way valve, the second non-return valve and the outlet.

5. Method according to claim 4, wherein the process liquid pressure p1 is above $2.0 \times 10^6$ Pa and the liquid pressure p4 inside the isolated chamber is $1.0 \times 10^6$ Pa or below during ultrasonic cavitation cleaning.

6. Method according to claim 4, wherein a cleaning agent is fed from a container to the chamber via the first three-way valve.

7. Method according to claim 4, wherein a fluid from the chamber is fed to a spill tank or pressure vessel via the first three-way valve.

8. Method according to claim 1, wherein some of the process liquid is fed into a side stream flow arrangement, wherein the process liquid isokinetically sampled comprising the following steps:
positioning of liquid analysis system with isokinetic coaxial sampling probe into a sampling port of subsea process line by means of an ROV;
sampling from subsea process line through isokinetic coaxial sampling probe;
feeding of process liquid to a first flow controller circulation pump, a two-way valve, chamber (C), three-way valve, a second flow controller circulation pump;
sealing the chamber (C) by means of valves;
reducing the pressure inside the chamber by means of piston system;
subjecting the optical window (W) to ultrasonic signals;
suspending ultrasound signals within the chamber (C) after a given period;
increasing the pressure inside the chamber (C) by means of piston system;
opening chamber (C) by means of valves;
feeding process liquid inside chamber (C) back to the subsea process line via the three-way valve, the second flow controller circulation pump and an outlet of the isokinetic coaxial sampling probe; and
retracting the liquid analysis system with isokinetic coaxial sampling probe from a sampling port of subsea process line by means of an ROV.

9. Method according to claim 8, wherein liquid pressure in the subsea process line is above $2.0 \times 10^6$ Pa and liquid pressure inside the sealed chamber is $1.0 \times 10^6$ Pa or below during ultrasonic cavitation cleaning.

10. Method according to claim 1, wherein measured optical properties in the process liquid are oil concentration, suspended solids, suspended oil, particulate matter and particle size.

11. System for ultrasonic cavitation cleaning of an optical window in an analysis system in a process line containing process liquid comprising:
a transducer module with an optical window (W) located adjacent to the process line and in association with a chamber;
at least one valve which isolates said chamber from said process line when closed and fluidly connects said chamber to said process line when open;
a piston connected to said chamber such that the pressure in said chamber is reduced when the at least one valve is closed and the piston is moved from a first position to a second position;
wherein the optical window (W) is located inside or can be moved into said chamber such that the optical window (W) of the transducer module can be isolated from the process line and subjected to ultrasonic emission from said transducer module when the valve is closed and when the pressure is reduced in said chamber.

12. System according to claim 11, wherein the process liquid pressure in process line is above $2.0 \times 10^6$ Pa and the pressure inside said isolated chamber is $1.0 \times 10^6$ Pa or below during ultrasonic cavitation cleaning.

13. System according to claim 11, wherein some of said process liquid is redirected by means of a side-stream flow arrangement comprising:
an inlet from the process line having a liquid pressure p1 at inlet;
a feed line from inlet, a first non-return valve, a first three-way valve, and a chamber having a pressure p3;
a transducer module connected to the chamber;
a second three-way valve downstream from the chamber, a piston system;
a feed line connecting the second three-way valve to a second non-return valve and back into the process line by means of an outlet wherein the process liquid has a pressure p2 at outlet, and the pressure drop from p1 to p2 is equal to p3;
wherein said transducer module comprises an optical window (W), an ultrasonic transducer, a fiber optic cable and a power cable connected to a sensor module comprising at least one light source, a computer, an imaging camera, a UV/fluorescence spectrometer, and a cable for remote communication.

14. System according to claim 13, wherein a feed line from a cleaning agent container is connected to the chamber via the first three-way valve.

15. System according to claim 13, wherein a feed line to a spill tank or pressure vessel is connected to the chamber via the first three-way valve.

16. System according to claim 11, for ultrasonic cavitation cleaning in a liquid analysis system wherein some of said process liquid is redirected by means of an isokinetically sampled side-stream flow arrangement comprising:
a retractable isokinetic coaxial sampling probe with an inlet extending into a sampling port of subsea process line by means of an ROV;
a first flow controller circulation pump downstream from the sampling probe, followed by a cleaning-mode bypass channel, a two-way valve, analysis chamber (C)

with optical window (W), a three-way valve, a variable control piston system, and a second flow controller circulation pump;

a feed line back to the sampling probe with an outlet to the subsea process line; and a module with an ultrasonic transducer, a full scan fluorescence spectrometer, microscope, video imaging camera, light sources, hardware for automatic control and PC remote control from top-side, and a cable for connection to top-side.

17. System according to claim 16, wherein a piston system is mechanically coupled to the analysis chamber (C) and is situated directly opposite from the optical window (W); and a second two-way valve is situated directly downstream from the analysis chamber (C).

18. System according to claim 17, wherein a pressure gauge is mechanically coupled to the analysis chamber and located between inlet and outlet valves connected to the analysis chamber.

* * * * *